United States Patent
Uchigaki et al.

(10) Patent No.: US 6,849,052 B2
(45) Date of Patent: Feb. 1, 2005

(54) BODY FLUID MEASURING APPARATUS WITH LANCET AND LANCET HOLDER USED FOR THE MEASURING APPARATUS

(75) Inventors: Takatoshi Uchigaki, Kyoto (JP); Katsumi Hamamoto, Kyoto (JP); Yasuhide Kusaka, Kyoto (JP)

(73) Assignee: Arkray, Inc., Kyoto (JP)

( * ) Notice: Subject to any disclaimer, the term of this patent is extended or adjusted under 35 U.S.C. 154(b) by 267 days.

(21) Appl. No.: 10/149,636

(22) PCT Filed: Dec. 13, 2000

(86) PCT No.: PCT/JP00/08835

§ 371 (c)(1),
(2), (4) Date: Jun. 12, 2002

(87) PCT Pub. No.: WO01/41643

PCT Pub. Date: Jun. 14, 2001

(65) Prior Publication Data

US 2002/0198444 A1 Dec. 26, 2002

(30) Foreign Application Priority Data

Dec. 13, 1999 (JP) ............................................. 11-353185

(51) Int. Cl.[7] .................................................. A61B 5/00
(52) U.S. Cl. ...................................... 600/584; 600/345
(58) Field of Search ................................ 600/573, 576, 600/583, 584, 345

(56) References Cited

U.S. PATENT DOCUMENTS

| | | | |
|---|---|---|---|
| 5,266,179 A | 11/1993 | Nankai et al. | |
| 5,746,217 A | * 5/1998 | Erickson et al. | ............ 600/573 |
| 5,916,230 A | 6/1999 | Brenneman et al. | |
| 6,048,352 A | * 4/2000 | Douglas et al. | ............ 600/583 |

FOREIGN PATENT DOCUMENTS

| | | |
|---|---|---|
| JP | 4-357452 | 12/1992 |
| JP | 09-266898 | 10/1997 |
| JP | 10-028683 | 2/1998 |
| JP | 10-166894 | 6/1998 |
| JP | 2000-217804 | 8/2000 |
| WO | WO 99/26539 | 6/1999 |

* cited by examiner

Primary Examiner—Eric F. Winakur
(74) Attorney, Agent, or Firm—Merchant & Gould P.C.

(57) ABSTRACT

A body fluid measuring apparatus, comprising a main body (20) and a lancet holder (30) installed on the main body (20), the lancet holder (30) further comprising a lancet (31) capable of being moved for piercing to allow body fluid to be bled from skin (S) and a biosensor (36) introducing the bled body fluid for a specified measurement, wherein the biosensor (36) is moved in a specified direction by a sensor moving mechanism (40, 42).

19 Claims, 12 Drawing Sheets

BODY FLUID MEASURING APPARATUS WITH LANCET AND LANCET HOLDER USED FOR THE MEASURING APPARATUS

TECHNICAL FIELD

The present invention relates to a body fluid measuring apparatus provided with a lancet, which is capable of sampling and measuring body fluid by a single operation for checking a substance contained therein such as the glucose concentration in blood (hereinafter referred to as "blood glucose level"). The present invention also relates to a lancet holder removably attached to such a body fluid measuring apparatus.

BACKGROUND ART

For diabetes treatment, the blood glucose level of a patient need be maintained in a normal range. Thus, the management of the blood glucose level by the patient himself or herself is important. Particularly, for keeping the blood glucose level in a normal range by insulin injection, measurement of the blood glucose level by the patient himself or herself is essential.

A portable blood glucose level measuring apparatus used for such a purpose is already commercially available, an example of which is disclosed in JP-A-4-357452. This blood glucose level measuring apparatus is used by inserting a disposable test piece provided with an enzyme electrode into a main body. When the test piece is brought into contact with blood as an analyte, a portion of the blood is introduced into a reacting portion by capillary action, thereby generating an anode current due to an enzyme reaction or an electrochemical reaction. In the apparatus, the anode current is converted to a blood glucose level, which is displayed.

In such a measuring apparatus as described above, the analyte, i.e. blood for contact with the test piece is generally sampled using an instrument called lancet as disclosed in JP-A-9-266898 for example. A lancet is a tool used for making a small hole (or making a cut) on the skin of a fingertip, for example, of a patient. The blood drawn from the hole thus formed is brought into contact with a predetermined portion of the test piece. Thus, the self-measurement of the blood glucose level can be performed relatively easily.

However, the conventional self-measurement of the blood glucose level is inconvenient in that the lancet for sampling blood as an analyte is separate from the measuring apparatus, so that the two tools need be carried. Moreover, it is necessary to separately perform the steps of injuring the skin with the lancet and of bringing the blood drawn from the cut into contact with the test piece. Therefore, there is still room for improvement in terms of the convenience of use. Particularly, in bringing the blood into contact with the test piece, a necessary amount of blood need be brought into contact with a predetermined portion of the test piece. Therefore, in the case where this step is performed by an untrained or week-sighted patient or where blood is drawn from an earlobe which cannot be observed by the patient himself or herself, it is not easy to bring the blood drawn from the cut into contact with the test piece quickly and properly.

Further, the test piece is designed to suck blood from a hole at the tip end of the test piece into the biosensor provided in the reacting portion by capillary action. Therefore, 3 to 5 $\mu l$ of blood need be brought into contact with the test piece to ensure that a necessary amount of blood reaches the reacting portion. If the amount of blood is insufficient or if a sufficient amount of blood is not deposited appropriately on a small area surrounding the tip hole of the test piece, the apparatus may suffer erroneous measurements. In particular, such a case is more likely to occur with respect to patients such as infants and the elderly who tend to suffer insufficient drawing of blood from a cut.

To solve the above-described problems, JP-A-10-28683 proposes a blood glucose level measuring apparatus provided with a lancet. With this apparatus, just by operating the lancet built in the apparatus to injure the skin, the blood drawn from the skin can be measured by a biosensor also built in the apparatus. However, the apparatus disclosed in this gazette still has room for improvement in terms of convenience, because, in use, the lancet needle and the biosensor need be individually set at predetermined positions in the apparatus.

For improving the convenience in use, the inventors of the present invention have proposed, in JP-A-10-166894, a lancet holder which integrates a lancet and a biosensor. According to this apparatus, the patient's action needed for measurement is simplified, thereby enhancing the convenience in use. Further, the reliability of measurement is enhanced while decreasing the amount of analyte necessary for measurement. However, the reliability of measurement with a small amount of analyte of not more than 1.0 $\mu l$ has not yet been satisfactory.

DISCLOSURE OF THE INVENTION

It is therefore an object of the present invention to provide a body fluid measuring apparatus provided with a lancet, which is capable of realizing high measurement reliability even with a small amount of analyte without deteriorating the convenience.

Another object of the present invention is to provide a lancet holder for use in such a body fluid measuring apparatus.

A body fluid measuring apparatus according to a first aspect of the present invention includes a main body and a lancet holder for attachment to the main body. The lancet holder includes a lancet movable for stabbing skin to draw body fluid, and a biosensor for introducing the body fluid drawn to perform predetermined measurement. The biosensor is moved in a predetermined direction by sensor moving mechanism.

The lancet holder may be provided as a disposable article of consumption. For measurement, the user attaches the lancet holder to the main body. While holding the body fluid measuring apparatus so that the tip end of the lancet holder is pressed against the skin, the lancet is moved back and forth by operating a lancet operating mechanism for example. Such a movement of the lancet makes a cut on the skin, from which body fluid (e.g. blood) is drawn. By keeping the holding state, the blood drawn is introduced into the biosensor for predetermined measurement. According to the present invention, the sensor moving mechanism moves the biosensor so that the biosensor can locate more close to the blood drawn. As a result, even a small amount of blood of 1.0 $\mu l$ for example can be duly introduced into the reacting portion of the biosensor, which considerably enhances the reliability of the measurement.

Preferably, the biosensor is shaped like a plate and internally formed with a body fluid path having an inlet end. The biosensor is formed with an operative electrode and a counterpart electrode facing the body fluid path at a position spaced from the inlet end. Since the biosensor is shaped like a plate as a whole, the body fluid path formed therein is small in volume, which is suitable for the measurement of a small amount of analyte. Further, in the case where the operative electrode and the counterpart electrode are formed on the upper surface of the plate-shaped biosensor, conduction is easily established between these electrodes and terminals of the main body.

Preferably, the body fluid measuring apparatus further comprises body fluid detecting means for detecting the drawn body fluid. The sensor moving mechanism moves the biosensor in the predetermined direction in response to a detection signal generated by the body fluid detecting means. In the case where the body fluid detecting means is provided, when the body fluid is not drawn, the biosensor is prevented from unnecessarily advancing. This is advantageous for avoiding a measurement failure.

According to one embodiment of the present invention, the body fluid detecting means comprises a pair of conductance measuring electrodes facing the body fluid path at the inlet end of the biosensor. The body fluid is detected by sensing conduction established between the conductance measuring electrodes due to the body fluid. Since the conductance measuring electrodes can be formed similarly to the operative electrode and the counterpart electrode and at the same time as forming such electrodes, the manufacturing cost can be reduced. Further, such a structure is convenient for establishing electrical connection between the conductance measuring electrodes and terminals of the main body.

According to another embodiment of the present invention, the body fluid detecting means is non-contact detection means for detecting existence of the body fluid without contacting the body fluid drawn. With this structure, when a sufficient amount of body fluid is not drawn, the biosensor is not contaminated. Therefore, the biosensor together with the lancet holder can be reused so that the wasting can be prevented. The non-contact detection means comprises a light source (e.g. a light emitting diode) for emitting light toward the skin, and a light receiving element (e.g. a photodiode) for receiving reflected light from the drawn body fluid.

Preferably, the biosensor comprises a base plate having an upper surface on which the operative electrode and the counterpart electrode are formed, a pair of spacers spaced from each other and disposed on the base plate, and a cover plate laminated on the spacers to bridge the spacers. The body fluid path is defined between the spacers.

Preferably, the body fluid path is formed with a reactive reagent layer.

Preferably, the sensor moving mechanism comprises an eccentric cam driven by a motor for rotation, and the eccentric cam pushes an edge of the biosensor.

Preferably, the main body includes a plurality of terminals for slidably contacting a plurality of electrodes formed on an upper surface of the biosensor, an electronic circuit connected to the plurality of terminals, a lancet operation mechanism for moving the lancet for stabbing, and a display for displaying a measurement result. It is preferable that each of the terminals preferably comprises an elastic connector pin.

Preferably, the biosensor is held inclined so that one edge is closer to the skin than an opposite edge, and the biosensor is movable along an inclined movement path. In this case, it is preferable that the sensor moving mechanism acts on the opposite edge of the biosensor.

The biosensor includes a first electrode facing the body fluid path at the inlet end, and a second electrode facing the body fluid path at an end opposite to the inlet end. The filling of the body fluid path with the body fluid is detected by measuring conductance between the first electrode and the second electrode. In this case, for decreasing the number of electrodes, it is preferable that the second electrode is one of the operative electrode and the counterpart electrode.

A lancet holder according to the second aspect of the present invention comprises a lancet which is movable for stabbing skin to draw body fluid, and a biosensor for introducing the body fluid drawn to perform predetermined measurement. The biosensor is supported for movement in a predetermined direction.

Other features and advantages of the present invention will become clearer from the detailed description given below with reference to the accompanying drawings.

BEST MODE FOR CARRYING OUT THE INVENTION

Preferred embodiments of the present invention will be described below with reference to the accompanying drawings.

Figure 1:
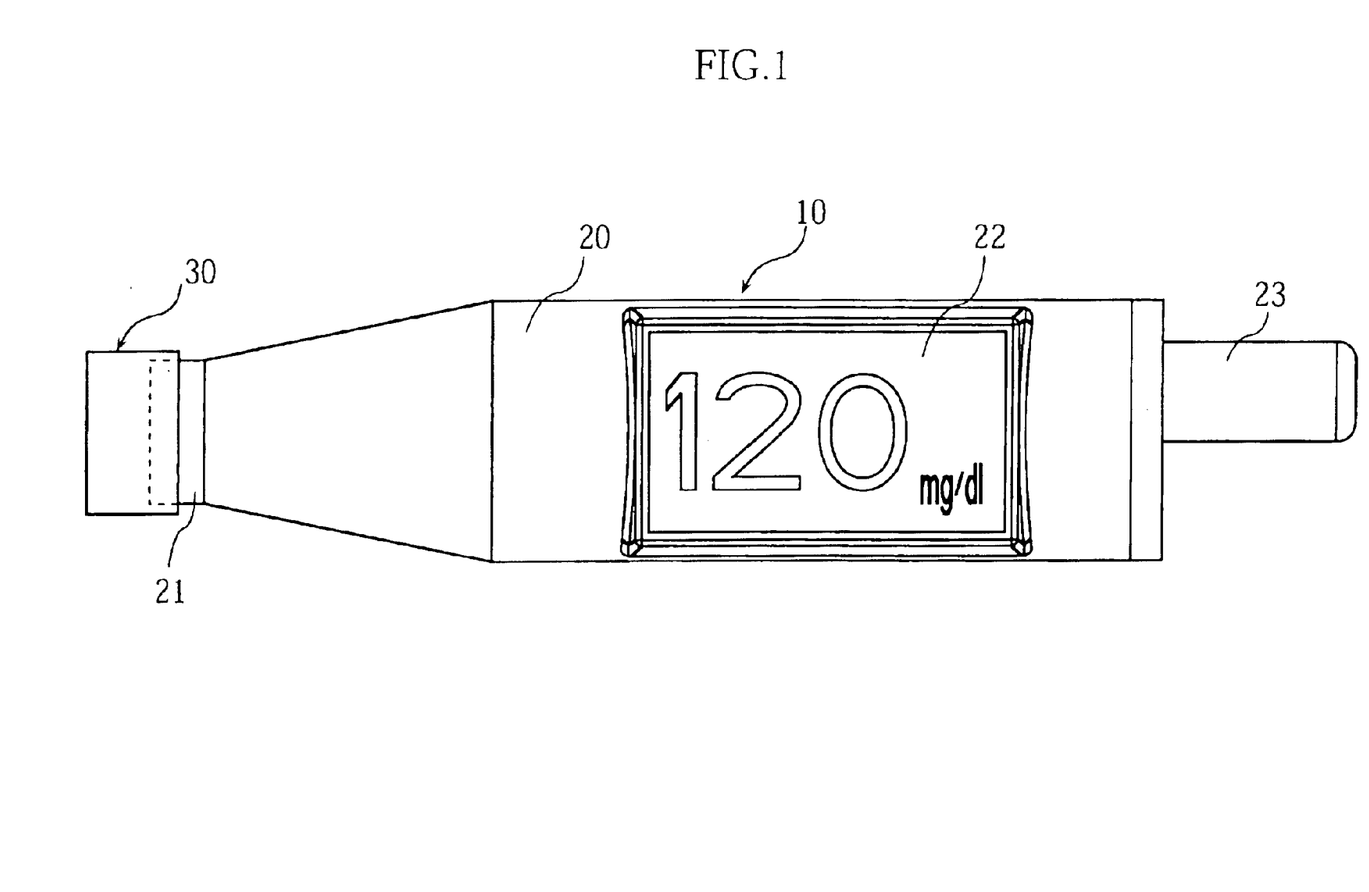
FIG. 1 is an overall view illustrating a body fluid measuring apparatus according to the present invention.
Figure 2:
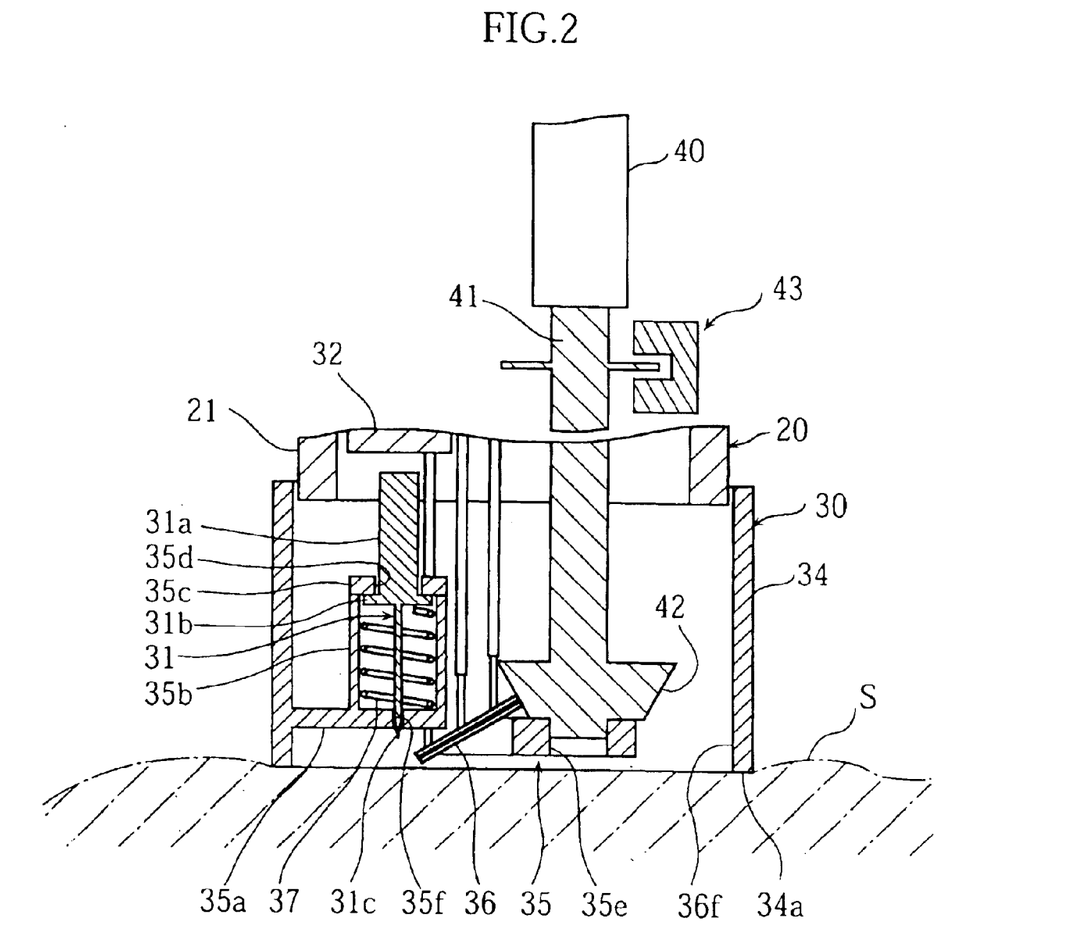
FIG. 2 is a sectional view taken along lines II—II in FIG. 5, illustrating a lancet holder in which a lancet and a biosensor are retreated.
Figure 3:
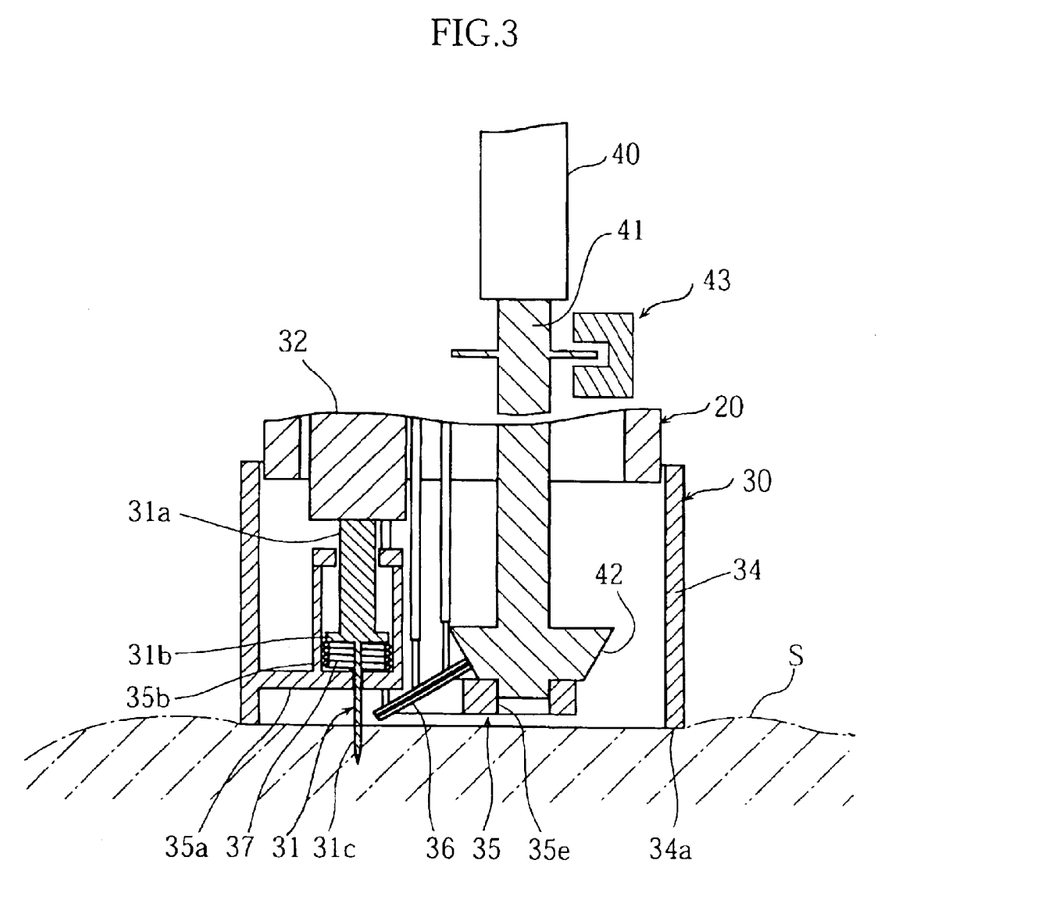
FIG. 3 is a sectional view similar to FIG. 2, illustrating a lancet which is advanced and a biosensor which is retreated.
Figure 6:
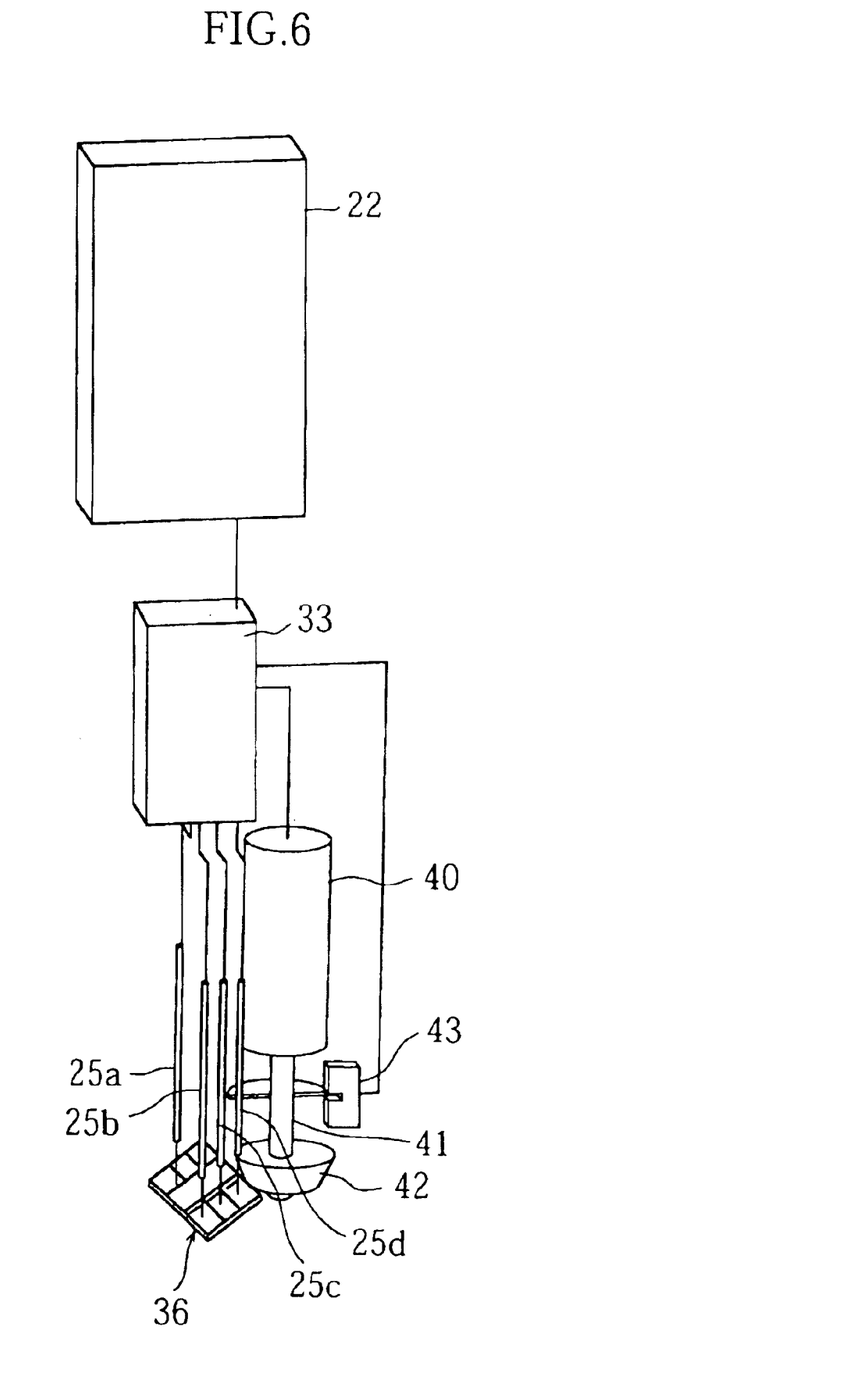
FIG. 6 is a schematic perspective view showing the internal structure of the main body.

As shown in FIGS. 1 through 3, a body fluid measuring apparatus 10 according to a preferred embodiment of the present invention is used with a lancet holder 30 fitted to a cylindrical tip end 21 of a main body 20. The main body 20 has an outer surface provided with a display 22 and may incorporate a small speaker (not shown) for vocally reporting the measurement result to the user. Further, the main body 20 incorporates a lancet operation mechanism for advancing a lancet 31 held by the lancet holder 30, a sensor moving mechanism for advancing a biosensor 36, and an electronic circuit 33 (See FIG. 6) such as a microcomputer.

The lancet operation mechanism for advancing the lancet 31 comprises a pushing rod 23 projecting from the rear end of the main body 21 for manual pushing by the user, and a connection rod 32 connected to the pushing rod 23 for movement following the pushing rod 23. The sensor moving mechanism for advancing the biosensor 36 comprises a motor 40 and an eccentric cam 42 fixed to a rotational shaft 41 of the motor 40.

Figure 5:
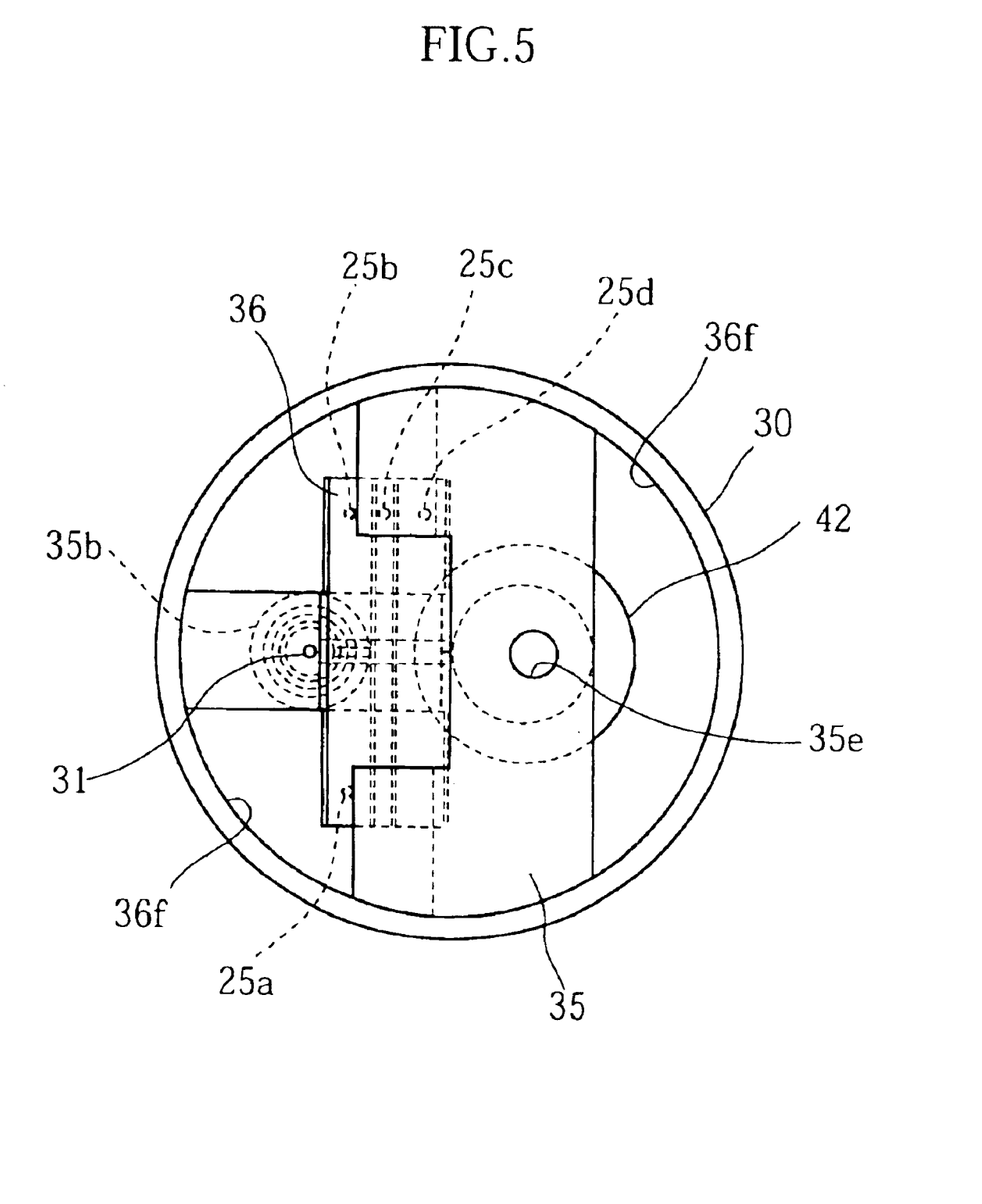
FIG. 5 is a bottom view of the lancet holder.

FIGS. 2 and 5 illustrate an example of lancet holder 30. The illustrated lancet holder 30 has a cap-like configuration comprising a cylindrical wall 34 and a bottom wall 35 partially closing the end of the cylindrical wall 34. The cylindrical wall 34 and the bottom wall 35 are formed by molding a resin. The cylindrical wall 34 has an inner diameter corresponding to the outer diameter of the cylindrical tip end 21 of the main body 20 for easy attachment and detachment relative to the cylindrical tip end 21. The cylindrical wall 35 has a lower end 34a which, in use, comes into contact with the user's skin S.

The cap-shaped lancet holder 30 incorporates the lancet 31 and the biosensor 36. The bottom wall 35 includes a thin-walled portion 35a from which a cylindrical housing 35b stands. The cylindrical housing 35b has an upper end closed with a lid 35c. The lid 35c is formed with a central hole 35d.

The lancet 31 includes a guide shaft 31a slidably fitted into the central hole 35d, a flange 31b formed at the lower end of the guide shaft 31, and a stabbing needle 31c projecting from the flange 31b. The guide shaft 31a and the flange 31b are formed by molding a resin and integral with each other. The stabbing needle 31c, which is formed of a metal, is inserted integrally together with the resin molding. The lancet 31 is normally biased toward a retreated position (the position at which the flange 31b contacts the lid 35c) shown in FIG. 2 by an elastic member 37 arranged in the housing 35b in contact with the flange portion 31b. At the retreated position, the upper end of the guide shaft 31a projects inwardly from the lid 35c, whereas the stabbing needle 31c retreats from the lower end 34a of the cylindrical wall 34. The thin-walled portion 35a of the lancet holder 30 is formed with a round hole 35f. The stabbing needle 31c advances and retreats through the round hole 35f.

In the illustrated embodiment, the elastic member 37 is a compression coiled spring formed of a metal or a resin. Alternatively, the elastic member may be formed of a resilient material such as foamed urethane. In the case where the elastic member 37 is made of foamed urethane, the stabbing needle 31c is embedded in the foamed urethane when the lancet 31 is at the retreated position so that the stabbing needle is less likely to be contaminated. Further, the elastic member 37 may be a leaf spring integrally formed on the guide member 31a formed of a resin.

Figure 7:
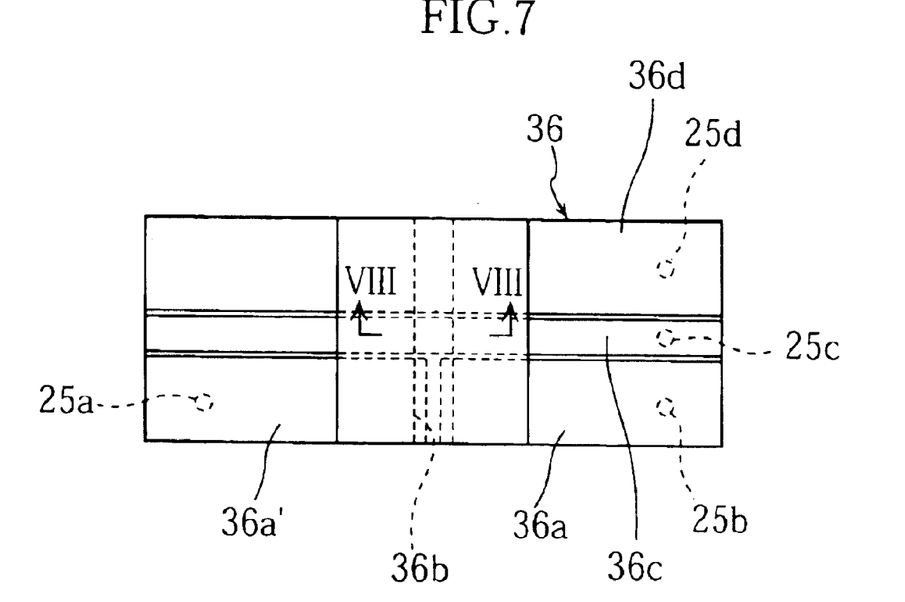
FIG. 7 is a plan view of the biosensor.

The plate-like biosensor 36 is slidably supported, as inclined, by the bottom wall 35 of the lancet holder 30 adjacent to the lancet 31. As shown in FIGS. 7 and 9, the biosensor 36 has an elongated rectangular configuration. The biosensor 36 includes an insulating base plate 361, a pair of plate-shaped spacers 362, 362' laminated on the insulating base plate 361, and a plate-shaped cover 363 further laminated on the plate-shaped spacers 362, 362'. The insulating base plate 361 has an upper surface formed with a pair of conductance measuring electrodes 36a, 36a', an operative electrode 36c and a counterpart electrode 36d. The insulating base plate 361, the two plate-shaped spacers 362, 362' and the plate-shaped cover 363 define a body fluid path 36b (See FIG. 8). Part of the conductance measuring electrodes 36a, 36a', part of the operative electrode 36c and part of the counterpart electrode 36d face the body fluid path 36b. The body fluid path 36b accommodates a reaction reagent portion 36e.

The biosensor 36 may be manufactured as follows. First, as shown in FIG. 9, an elongated rectangular base plate 361 is prepared from an insulating resin sheet having a thickness of 0.2 mm for example.

Subsequently, conductance measuring electrodes 36a, 36a', an operative electrode 36c, and a counterpart electrode 36d are formed on an upper surface of the base plate 361 as film strips extending longitudinally of the base plate 36a by screen-printing a graphite ink. The conductance measuring electrodes 36a, 36a', the operative electrode 36c, and the counterpart electrode 36d may be alternatively provided by forming a film of noble metal such as gold, palladium or platinum by vapor deposition to entirely cover the upper surface of the base plate 361 and then etching the metal film into a predetermined pattern.

Subsequently, a pair of rectangular spacer plates 362, 362' are disposed on the base plate 361 while keeping a spacing therefrom which is slightly larger than the spacing between the two conductance measuring electrodes 36a and 36a'. Each spacer plate 362, 362' may be a resin plate having a thickness of 0.2 mm for example and fixed to the base plate 361 with a double-sided adhesive tape for example. The body fluid path 36b may be 1.0 mm in width, 3 mm in length and 0.2 mm in depth (which is equal to the thickness of the spacer plates 362, 362') for example.

Figure 8:
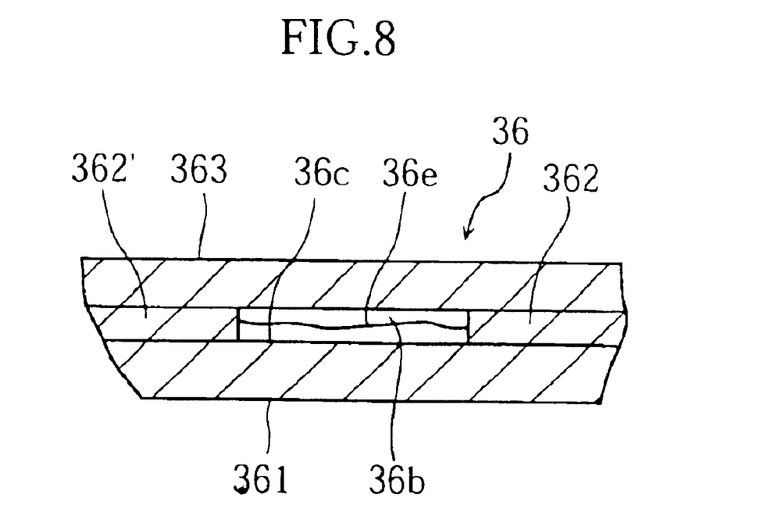
FIG. 8 is a sectional view taken along lines VIII—VIII of FIG. 7.
Figure 9:
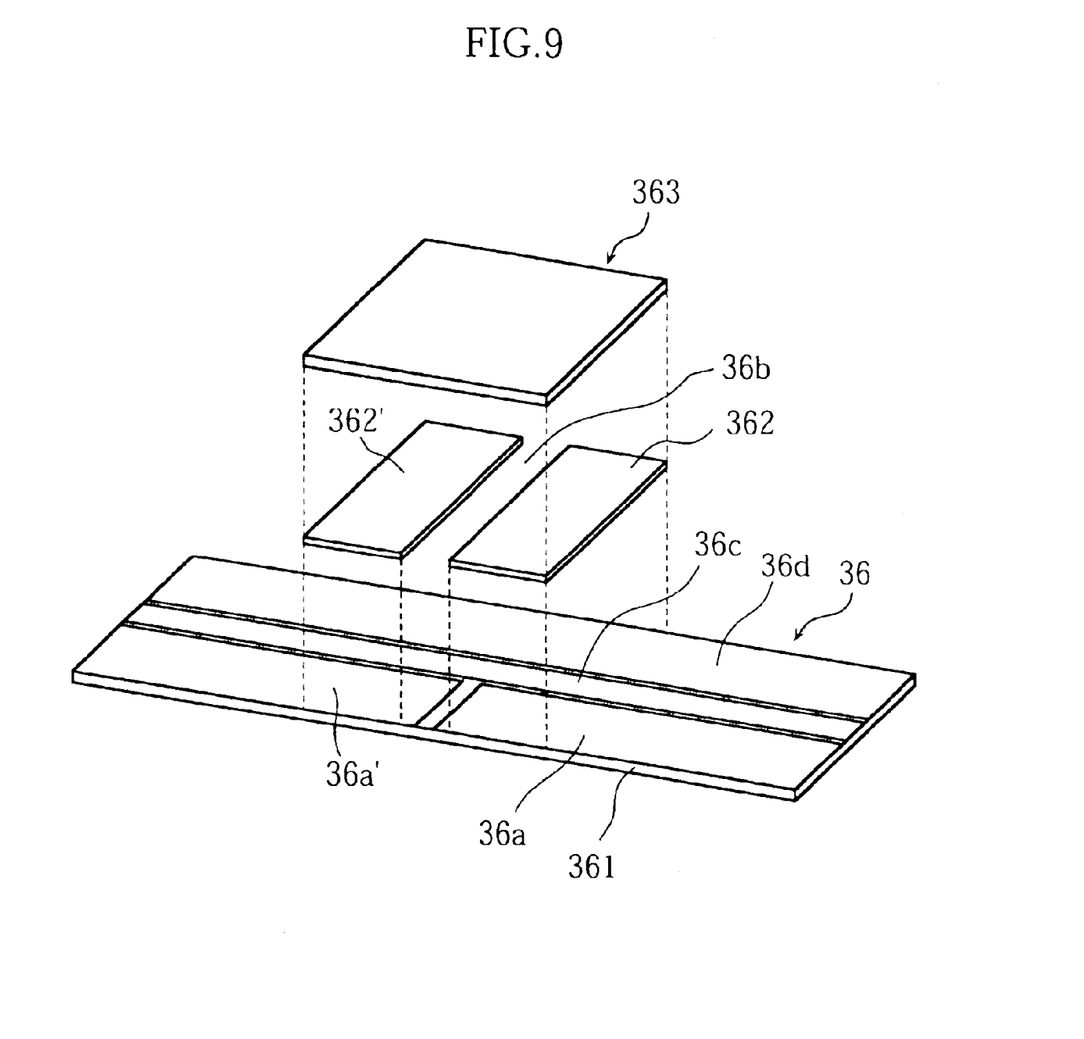
FIG. 9 is an exploded perspective view of the biosensor.

Then, as clearly shown in FIG. 8, a reactive reagent layer 36e is formed in the body fluid path 36b by the dispensing method for example. In the case where the biosensor 36 is used for measuring the blood glucose level, the reactive reagent layer 36e contains glucose oxidase which is an oxidization enzyme, and potassium ferricyanide as a mediator.

Subsequently, as shown in FIG. 9, a rectangular cover plate 363 is attached to cover the spacer plates 362, 362', thereby completing the biosensor 36. As a result, the body fluid path 36b is upwardly closed by the cover plate 363. However, the body fluid path 36b is open at the opposite ends thereof for allowing body fluid (blood) to enter the body fluid path 36b due to capillary action for reaction with the reactive reagent layer 36e. The body fluid path 36b of the above dimensions has a volume of 0.6 μl, which is found by 1.0 mm×3 mm×0.2 mm. By subtracting, from this value, 0.2 μl which is the approximate solid volume of the reactive reagent layer 36e, it is found that the body liquid flow path 36b has an extremely small net volume of about 0.4 μl.

As clearly shown in FIG. 2, the plate-like biosensor 36 is supported, as inclined, by the bottom wall 35 of the lancet holder 30 so that the stabbing needle 31c is located adjacent to the conductance measuring electrodes 36a, 36a'. The biosensor 36 is so inclined that the side formed with the conductance measuring electrodes 36a, 36a' is closer to the user's skin than the counterpart electrode 36d.

Figure 4:
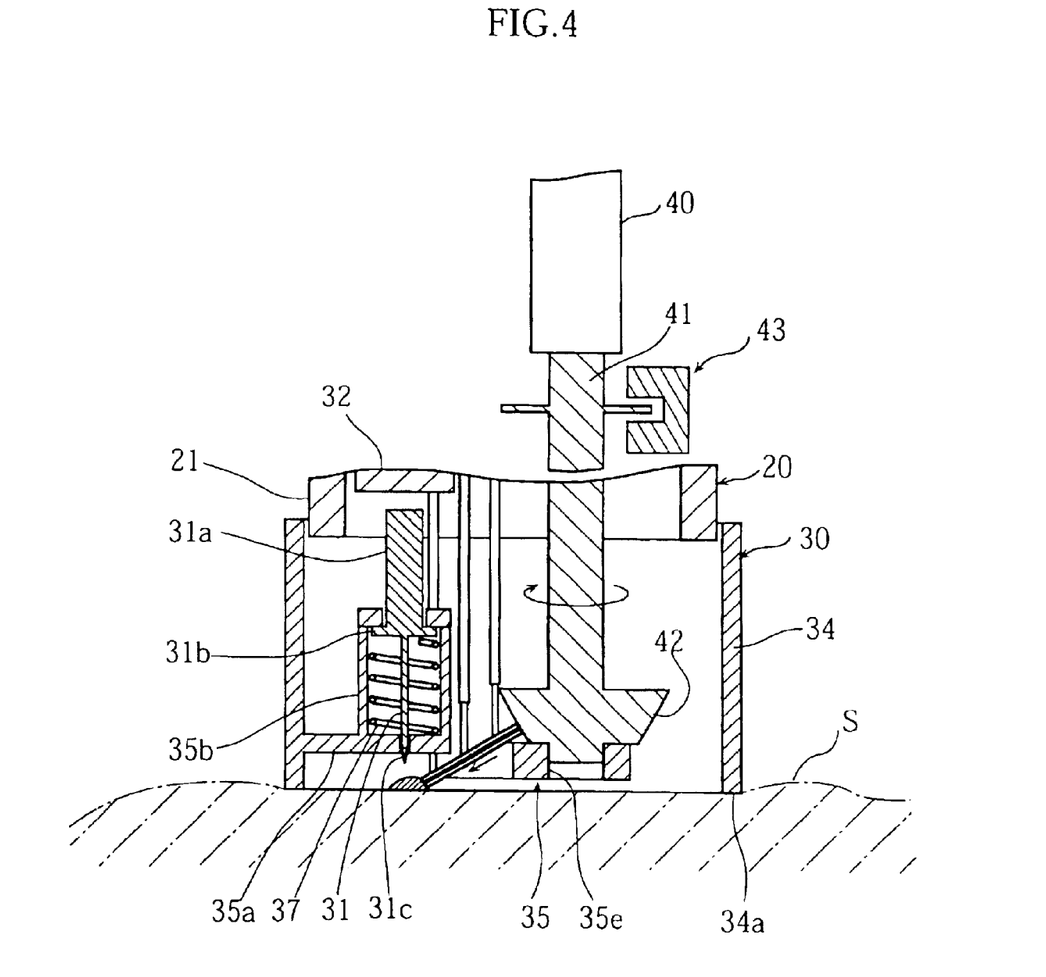
FIG. 4 is an enlarged sectional view illustrating a lancet which is retreated and a biosensor which is advanced.

The biosensor 36 is slidably movable to approach the stabbing needle 31c by the sensor moving mechanism 40 which will be described later. As shown in FIGS. 4 and 5, the bottom wall 35 of the lancet holder 30 is formed with a round hole 35e for fitting to the lower end of the rotational shaft 41 of the motor 41. Thus, when the lancet holder 30 is attached to the main body 20, the rotational center of the eccentric cam 42 is precisely determined. Further, the bottom wall 35 of the lancet holder 30 is formed with a pair of arcuate openings 36f (See FIG. 5) sandwiching the biosensor-supporting region. By the provision of the openings 36f, a negative pressure generating mechanism for example may be provided in the main body for exerting a negative pressure to the skin while holding the cylindrical wall 34 of the lancet holder 30 in contact with the skin S.

As shown in FIGS. 4 through 7, the cylindrical tip end 21 of the main body 20 is provided with four pin connectors 25a, 25b, 25c, 25d each having a tip end projecting from the cylindrical end 21 into the lancet holder 30. The pin connectors 25a–25d individually and elastically contact the exposed portions (i.e. portions which are not covered with the cover 363) of the electrodes 36a, 36a' 36c 36d of the biosensor 36. The pin connectors 25a–25d are connected to the electronic circuit 33 (See FIG. 6). The electronic circuit 33, which may comprise a microcomputer, has a function of determining the value of an analyte such as the blood glucose level from the current generated due to enzyme reaction or electrochemical reaction in the biosensor 36 by utilizing the calibration curve, a function of displaying the determined value at the display 22 of the main body 20, and a function of controlling the sensor moving mechanism 40 for moving the biosensor 36.

In the illustrated embodiment, the eccentric cam 42 driven by the motor 41 for rotation includes a bevel surface. When the lancet holder 30 is attached to the body 20, the bevel surface comes into contact with an edge of the biosensor 36 (the edge which is opposite to the edge formed with the conductance measuring electrodes 36a, 36a'). The degree of eccentricity of the cam 41 is set in accordance with the stroke for moving the biosensor 36 (e.g. 0.1–0.5 mm). The rotational initial position of the cam 42 is detected by a rotary encoder 43.

In use, the body fluid measuring apparatus 10 having the above structure operates in the manner described below.

The lancet holder 30 is supplied as a disposable article of consumption. In using the body fluid measuring apparatus 10, the user attaches the lancet holder 30 to the cylindrical portion 21 of the main body 20 (See FIG. 1). Since the lancet holder 30 is shaped like a cap in the illustrated embodiment, the attaching operation can be performed easily. As shown in FIG. 2, by the attachment of the lancet holder 30, the connector pins 25a, 25b, 25c, 25d on the side of the main body 20 automatically come into contact with the electrodes 36a, 36a', 36c, 36d of the biosensor 36.

Subsequently, with the lower end 34a of the cylindrical wall 34 of the lancet holder 30 pressed against an appropriate portion of the user's skin such as a fingertip or an earlobe, the pushing portion 23 is pushed down. As a result, the pushing rod 32 within the main body 20 pushes the guide shaft 31a of the lancet 31 to advance the lancet 31 against the elastic force of the elastic member 37 until the pushing rod 32 comes into contact with the lid 35c of the lancet holder 30. At this time, the stabbing needle 31c of the lancet 31 passes adjacent to the inlet of the body fluid path 36b of the biosensor 36 to project from the lower end 34a of the cylindrical wall 34 by a predetermined length (the state shown in FIG. 3). When the pushing portion 23 is relieved, the pushing rod 32 is restored to its original position by the elastic force of the spring. Further, due to the elastic force of the elastic member 37, the lancet 31 also returns to its retreated position where the stabbing needle 31c retreats from the lower end 34a of the cylindrical wall 34 (the state shown in FIG. 2).

The projection of the stabbing needle 31c makes an appropriate cut on the skin S to draw blood B, which is introduced to the inlet of the body fluid path 36b of the biosensor 36 by capillary action. At the moment when the blood enters the inlet of the body fluid path 36b of the biosensor 36, current flows across the paired conductance measuring electrodes 36a, 36a' so that a signal is generated due to the change of the conductance. In response to the signal, the motor 41 drives the biosensor 36 through the eccentric cam 42 for forward movement. This prompts the blood to be sucked into the body fluid path 36b.

As described above, since the net volume of the body fluid path 36b in the biosensor 36 is extremely small and the biosensor 36 is advanced toward the blood, the body fluid path 36b is reliably filled with a small amount of blood. Therefore, blood can be introduced into the body fluid path 36b in an amount just necessary for the measurement simply by conducting the above operation while keeping the lancet holder 30 pressed against the skin S for a predetermined period of time. Thus, it is not necessary to visually monitor the amount of blood drawn. As described before, a negative pressure generating mechanism such as a suction cylinder may be provided in the main body to apply a negative pressure to the skin S through the openings 36f of the lancet holder 30. In such a case, a cut is formed on the skin in a congestive state by the stabbing needle 31c so that a required amount of blood is more reliably drawn.

Figure 10:
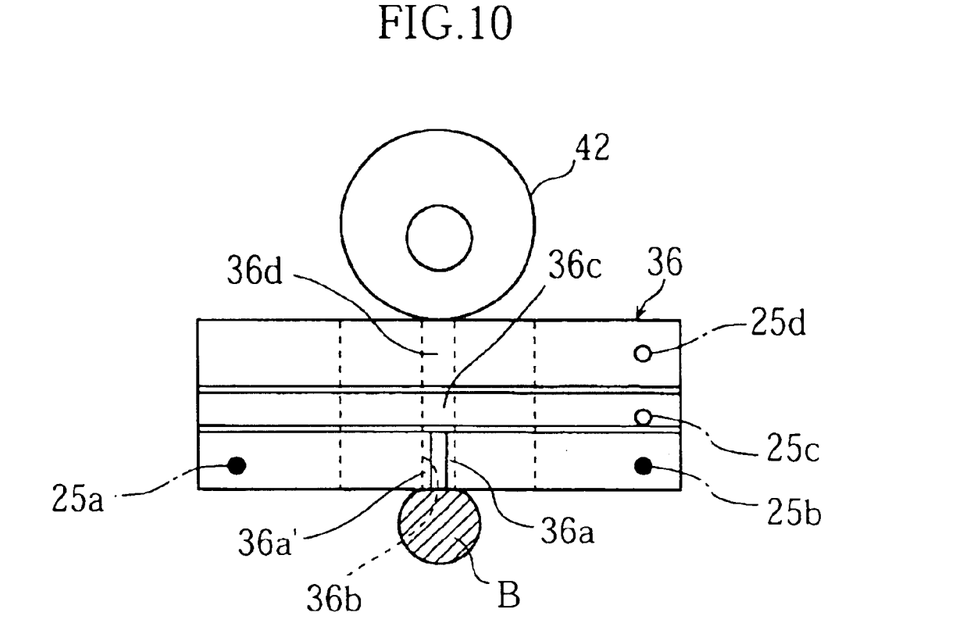
FIGS. 10–12 illustrate the operation of the biosensor.
Figure 11:
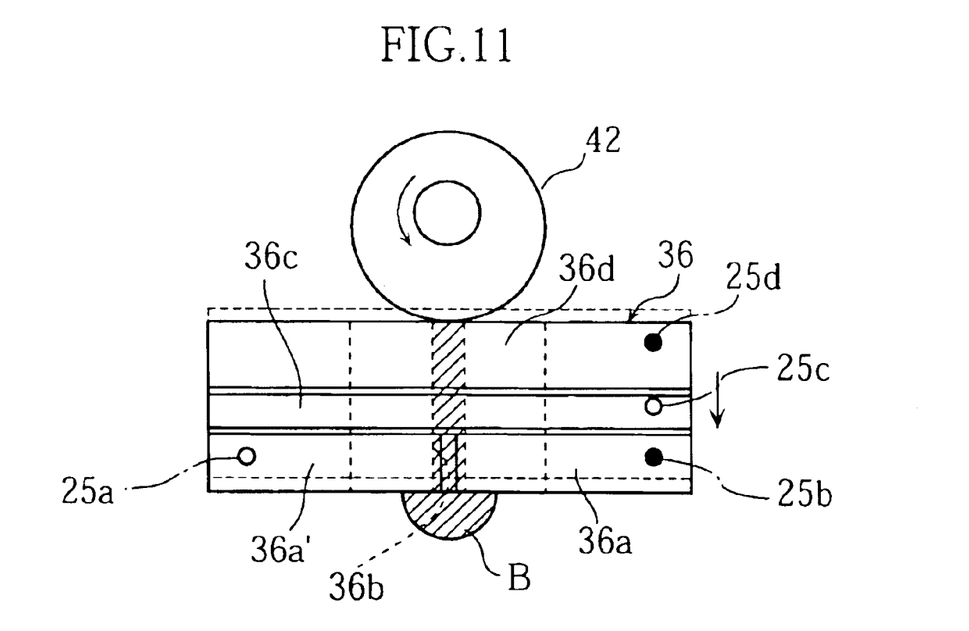
Figure 12:
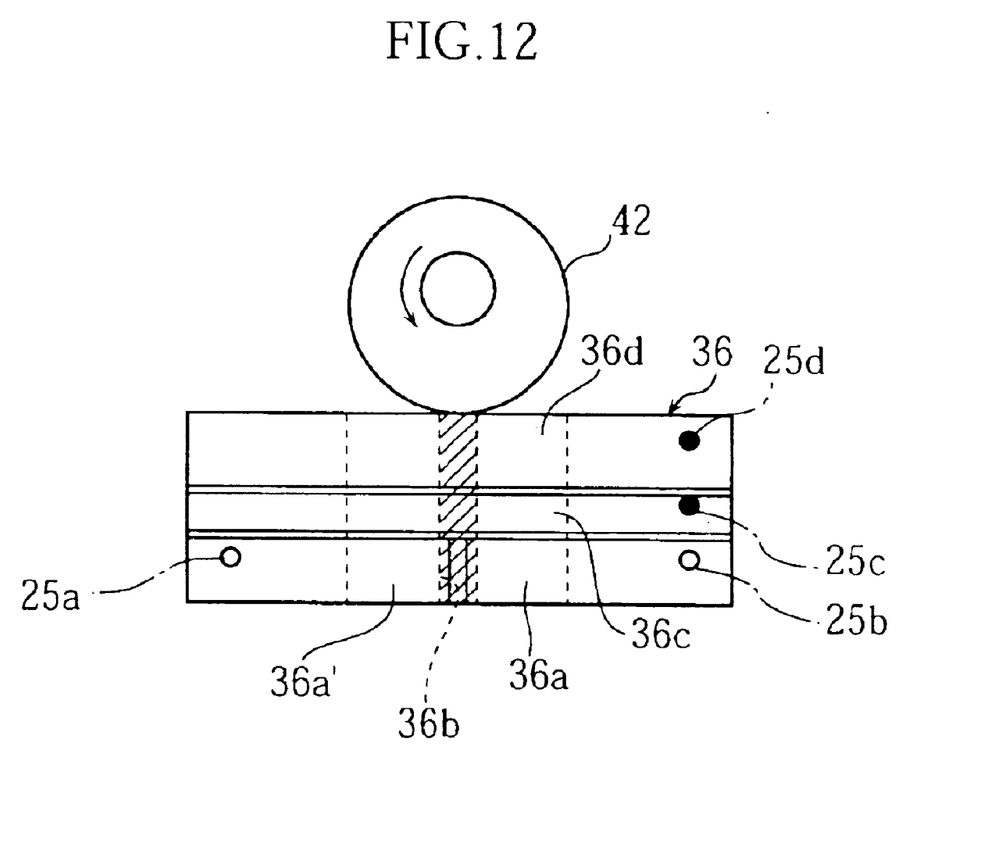
Figure 13:
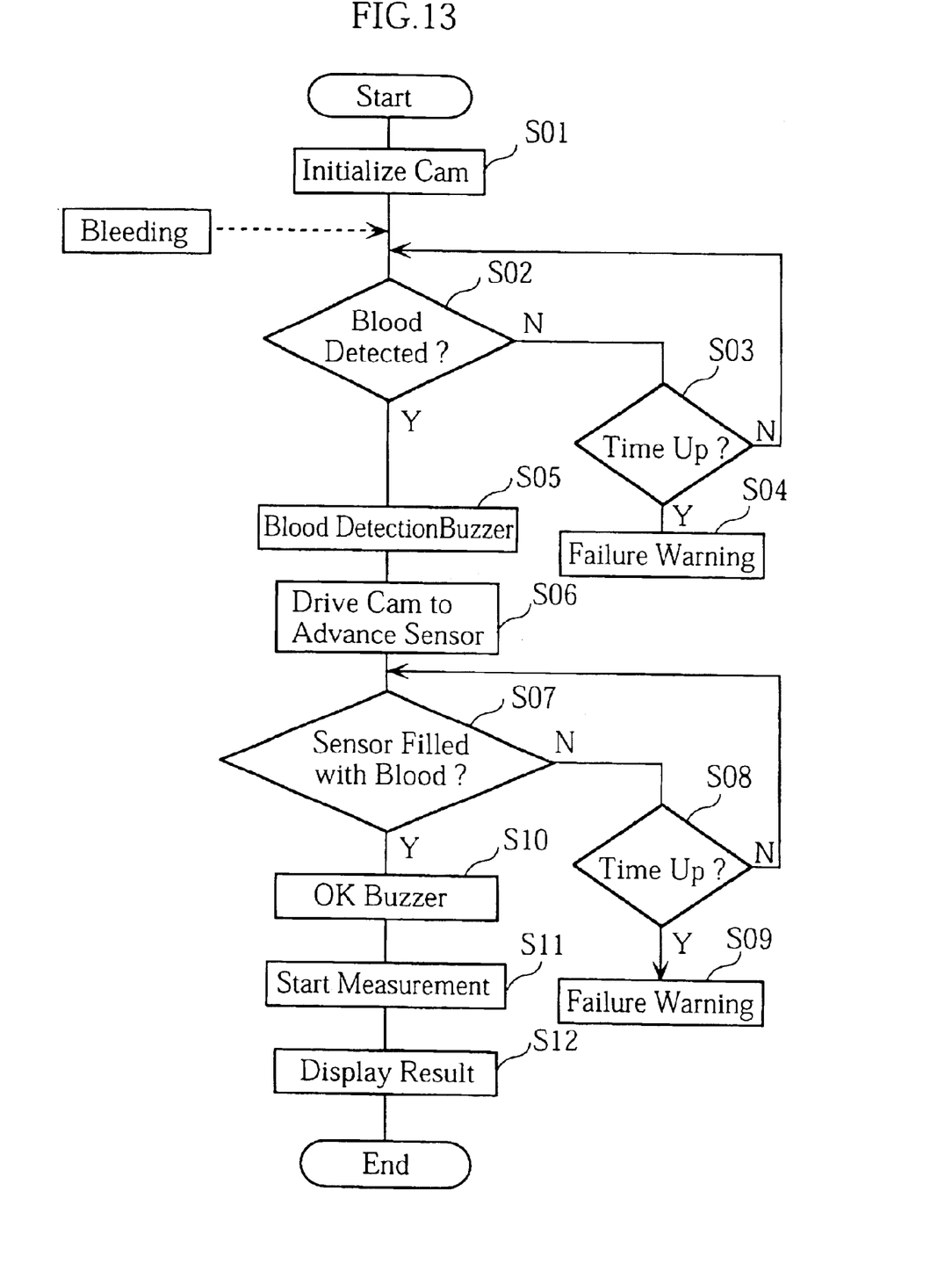
FIG. 13 is a flowchart illustrating an example of process for controlling the sampling and measuring of the body fluid.

Next, with reference to the operational figures of FIGS. 10–12 and the flowchart of FIG. 13, the operation of the apparatus will be described in more detail by showing an example of the controlling operation by the electronic circuit 33.

First, when the switch of the main body is turned on, the position of the eccentric cam 42 is initialized (S01). At this time, as shown in FIGS. 2 and 10, the biosensor 36 is located at the most retreated position. The initialized state is detected by the rotary encoder 43.

In this state, the user conducts the bleeding operation by holding the apparatus with the lancet holder 30 pressed against the skin S and operating the lancet 31 in the above-described manner (FIG. 3). As described before, since the inlet of the body fluid path 36b of the biosensor is arranged close to the lancet 31 in advance, the blood B drawn from the skin contacts the inlet of the body fluid path 36b. This state is detected due to a change in the resistance between the two conductance measuring electrodes 36a, 36a'. Specifically, whether the bleeding has occurred or not is determined by measuring the resistance between the pin connectors 25a and 25b corresponding to the conductance measuring electrodes 36a, 36a' (S02).

If bleeding is not detected within a predetermined period of time (S02: NO, S03: YES), a failure warning is given vocally or by displaying (S04) to urge the user to retry.

If the bleeding is detected (S02: YES), the bleeding is reported vocally for example (S05), and the eccentric cam 42 is driven to advance the biosensor 36 (S06). Thus, as shown in FIGS. 4 and 11, the biosensor 36 is moved so that the inlet of the body fluid path 36b projects into the drawn blood. As a result, the blood is reliably introduced into the body fluid path 36b due to capillary action. As described before, the biosensor 36 is so inclined that the inlet of the body fluid path 36b is closer to the skin whereas the opposite side is farther from the skin. This arrangement prevents the reverse surface of the advanced biosensor 36 from contacting the skin, thereby preventing the blood from reaching the reverse surface of the sensor. Thus, the waste of blood can be prevented.

Subsequently, it is determined whether the body fluid path 36b is filled with the blood (S07). As shown in FIG. 11, this may be performed, for example, by measuring the resistance between one of the conductance measuring electrodes 36a, 36a' and the counterpart electrode 36d. This is because, when the body fluid path 36b is filled with blood, a current flows across these electrodes.

If the body fluid path 36b is not filled with the blood within a predetermined period of time (S07: NO, S08: YES), a failure warning is given vocally or by displaying (S09) to urge the user to retry.

If it is determined that the body fluid path 36b is filled with blood (S07: YES), a notice is given vocally or by displaying that the apparatus may be removed from the skin S for example (S10). Thus, the measurement starts in S11 (See FIG. 12), and the result is displayed (S12) to terminate the process.

When the reactive reagent layer 36e is dissolved in the blood in the body fluid path 36b in the biosensor 36, an enzyme reaction starts, as represented by the formula (1) given below. As a result, potassium ferricyanide contained in the reactive reagent layer 36e is reduced to cumulatively produce potassium ferrocyanide which is a reduced-type electron carrier.

(1)

The amount of potassium ferrocyanide is proportional to the concentration of the substrate, i.e., the glucose concentration in the blood. The reduced-type electron carrier produced in a predetermined time is oxidized by the electrochemical reaction represented by the following formula (2).

(2)

The electronic circuit 33 in the main body 20 of the measuring apparatus 10 performs calculation to determine the glucose level (blood glucose level) based on the detected operative electrode current and displays the result on the LCD display 22 provided at the main body 20.

In this way, with the body fluid measuring apparatus 10 according to the present invention, it is possible to perform body fluid measurement such as blood glucose level measurement just by performing the preparation step of placing the lancet holder 30 at a predetermined portion of the main body 20 and the bleeding step of advancing the lancet 31 while keeping the tip end of the lancet holder 30 pressed against a fingertip or earlobe of the patient. Therefore, it is not necessary to separately perform, after the bleeding step, a measuring step by using other measuring instrument than the lancet. Further, since the biosensor 36 is advanced after the bleeding, the measurement can be reliably performed even with a small amount of blood.

As is clear from the above description, the gist of the present invention lies in that the body fluid measuring apparatus 10 comprises a disposable lancet holder 30 which integrates both a biosensor 36 and a lancet 31 and which is attached to the main body 20, whereby the lancet 31 causes bleeding of body fluid (blood) toward which the biosensor 36 is advanced for causing the sensor 36 to be internally filled with the bleeding fluid. Therefore, all the modifications within such a spirit are included in the scope of the present invention. Although some of the possibilities of modification have already been described, other modifications are also possible, as described below.

In the above embodiment, the biosensor 36 progresses from the retreated position to the advanced position in one step. However, the biosensor 36 may progress in two steps. Specifically, the biosensor 36 is initially held at the retreated position which is spaced from the lancet 31 by a certain distance. After the stabbing operation by the lancet 31, the biosensor 36 may be advanced to a detection position for detecting the blood drawn. Then, after the detection of the blood, the biosensor 36 may be further advanced to the most advanced position.

Figure 14:
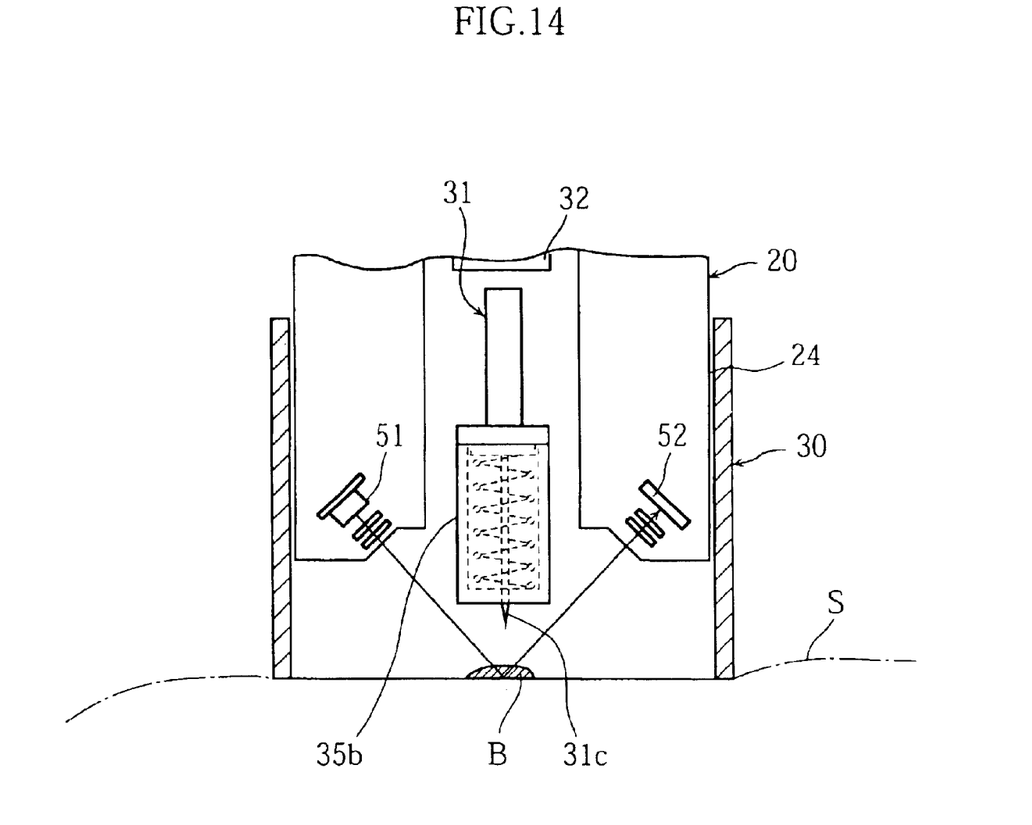
FIG. 14 is a sectional view showing a principal portion according to another embodiment.

In the above embodiment, blood is detected by measuring the conductance (resistance) between the conductance measuring electrodes 36a, 36a' at the inlet of the body fluid path 36b of the biosensor 36. However, the blood may be detected by non-contact detection means. For example, as shown in FIG. 14, the main body 20 may be provided with optical detection means including a light emitting element 51 for emitting light toward the skin S and a light receiving element 52 for receiving light reflected by the skin S. Thus, whether or not blood is properly drawn may be determined by measuring the amount of light of particular wavelength range (e.g. red light) received by the light receiving element 52. In this case, the light emitting element 52 may be a light emitting diode (LED) or a laser generator. As another example of optical detection means, the blood image on the skin may be captured by a small CCD camera and the size of a region having a particular color may be measured and computed to detect the bleeding state. Further, instead of the optical detection means, detection means utilizing ultrasonic waves may be employed. In the case where such non-contact detection means is used, the bleeding can be confirmed without contaminating the biosensor, thereby avoiding wasting of the biosensor.

According to the present invention, however, the drawing of the blood need not necessarily be confirmed. Therefore, on the assumption that the pushing of the lancet 31 inevitably causes bleeding, the biosensor 36 may be advanced when a predetermined period of time has passed after the pushing of the lancet 31.

In the illustrated embodiment, the lancet operation mechanism includes a pushing portion 23 for manual operation and a pushing rod 32 movable together with the pushing portion 23 so that the lancet 31 normally biased toward the retreating direction by the elastic member 37 (compression coil spring) is pushed forward (See FIGS. 2 and 3). Alternatively, though not illustrated, a lancet 31 may constantly be latched at a retreated position as elastically biased in the advancing direction so that the lancet 31 hits the skin by a resilient elastic force when the latch is manually released.

Further, as the sensor moving mechanism for moving the biosensor 36, use may be made of a solenoid, a piezoelectric element, shape-memory alloy, or a spring instead of the motor-driven eccentric cam 42 of the above embodiment.

In the illustrated embodiment, the elastic pin connectors 25a–25d provided in the main body 20 are electrically connected to the electrodes of the biosensor 36 when the lancet holder 30 is attached to the main body 20. Instead of this, pin connectors, which are normally retreated within the main body 20, may project from the main body 20 for contact with the electrodes of the biosensor in response to the attachment of the lancet holder 30 to the main body 20.

In the illustrated embodiment, the body fluid measuring apparatus 10 is described as an apparatus for measuring the blood glucose level. However, the measurement is not limited to the blood glucose level. Further, the specific design of the lancet holder 30 and the biosensor 36 may be varied in various ways. For example, the biosensor 36 may be provided with a reagent pad which exhibits color reaction upon contacting an analyte (body fluid), and the degree of the color reaction is optically measured. In this case, the detection of the body fluid bleeding from the skin is preferably performed optically. After the existence of the body fluid is detected, the biosensor is moved to a position for contacting the body fluid. After the body fluid is duly introduced to the reagent pad, the degree of reflection of the light emitted from the light source to the reacting portion is optically measured.

What is claimed is:

1. A body fluid measuring apparatus comprising:
a main body; and
a lancet holder for attachment to the main body;
wherein the lancet holder includes a lancet movable for stabbing a skin to draw body fluid, and a biosensor for introducing the drawn body fluid to perform predetermined measurement; and
wherein a sensor moving mechanism including a motor is further provided for moving the biosensor in a predetermined direction.

2. The body fluid measuring apparatus according to claim 1, wherein the biosensor is shaped like a plate and internally formed with a body fluid path having an inlet end, the biosensor being formed with an operative electrode and a counterpart electrode facing the body fluid path at a position spaced from the inlet end.

3. The body fluid measuring apparatus according to claim 2, further comprising body fluid detecting means for detecting the drawn body fluid, the sensor moving mechanism moving the biosensor in the predetermined direction in response to a detection signal generated by the body fluid detecting means.

4. The body fluid measuring apparatus according to claim 3, wherein the body fluid detecting means comprises a pair of conductance measuring electrodes facing the body fluid path at the inlet end of the biosensor, the body fluid being detected by sensing conduction established between the conductance measuring electrodes due to the body fluid.

5. The body fluid measuring apparatus according to claim 3, wherein the body fluid detecting means is non-contact detection means for detecting existence of the body fluid without contacting the drawn body fluid.

6. The body fluid measuring apparatus according to claim 5, wherein the non-contact detection means comprises a light source for emitting light toward the skin, and a light receiving element for receiving reflected light from the drawn body fluid.

7. The body fluid measuring apparatus according to claim 2, wherein the biosensor comprises a base plate having an upper surface on which the operative electrode and the counterpart electrode are formed, a pair of spacers spaced from each other and disposed on the base plate, and a cover plate laminated on the spacers to bridge the spacers, the body fluid path being defined between the spacers.

8. The body fluid measuring apparatus according to claim 2, wherein the body fluid path is formed with a reactive reagent layer.

9. The body fluid measuring apparatus according to claim 2, wherein the biosensor includes a first electrode facing the body fluid path at the inlet end, and a second electrode facing the body fluid path at an end opposite to the inlet end, filling of the body fluid path with the body fluid being detected by measuring conductance between the first electrode and the second electrode.

10. The body fluid measuring apparatus according to claim 9, wherein the second electrode is one of the operative electrode and the counterpart electrode.

11. The body fluid measuring apparatus according to claim 1, wherein the sensor moving mechanism comprises an eccentric cam driven by the motor for rotation, the eccentric cam pushing an edge of the biosensor.

12. The body fluid measuring apparatus according to claim 1, wherein the main body includes a plurality of terminals for slidably contacting a plurality of electrodes formed on an upper surface of the biosensor, an electronic circuit connected to the plurality of terminals, a lancet operation mechanism for moving the lancet for stabbing, and a display for displaying a measurement result.

13. The body fluid measuring apparatus according to claim 12, wherein each of the terminals comprises an elastic connector pin.

14. The body fluid measuring apparatus according to claim 1, wherein the biosensor is held inclined relative to a longitudinal axis of the lancet, the biosensor being movable along an inclined movement path.

15. The body fluid measuring apparatus according to claim 14, wherein the sensor moving mechanism acts on the opposite edge of the biosensor.

16. A lancet holder comprising:
a lancet which is movable for stabbing a skin to draw body fluid; and
a biosensor for introducing the body fluid drawn to perform predetermined measurement;
wherein the biosensor is held inclined relative to a longitudinal axis of the lancet for movement along a movement path.

17. A body fluid measuring apparatus comprising:
a main body; and
a lancet holder for attachment to the main body;
wherein the lancet holder includes a lancet movable for stabbing a skin to draw body fluid, and a biosensor for introducing the drawn body fluid to perform predetermined measurement;
wherein a sensor moving mechanism is further provided for moving the biosensor in a predetermined direction; and
wherein the biosensor is shaped like a plate and internally formed with a body fluid path having an inlet end, the biosensor being formed with an operative electrode and a counterpart electrode facing the body fluid path at a position spaced from the inlet end.

18. A body fluid measuring apparatus comprising:
a main body; and
a lancet holder for attachment to the main body;
wherein the lancet holder includes a lancet movable for stabbing a skin to draw body fluid, and a biosensor for introducing the drawn body fluid to perform predetermined measurement;
wherein a sensor moving mechanism is further provided for moving the biosensor in a predetermined direction; and
wherein the main body includes a plurality of terminals for slidably contacting a plurality of electrodes formed on an upper surface of the biosensor, an electronic circuit connected to the plurality of terminals, a lancet operation mechanism for moving the lancet for stabbing, and a display for displaying a measurement result.

19. A body fluid measuring apparatus comprising:
a main body; and
a lancet holder for attachment to the main body;
wherein the lancer holder includes a lancet movable for stabbing a skin to draw body fluid, and a biosensor for introducing the drawn body fluid to perform predetermined measurement;
wherein a sensor moving mechanism is further provided for moving the biosensor in a predetermined direction; and
wherein the biosensor is held inclined relative to a longitudinal axis of the lancet, the biosensor being movable along an inclined movement path.

* * * * *